United States Patent
Jautelat et al.

Patent Number: 5,482,955
Date of Patent: Jan. 9, 1996

[54] CYCLOPROPYL-ETHYL-AZOLES

[75] Inventors: Manfred Jautelat, Burscheid; Stefan Dutzmann, Hilden; Klaus Stenzel, Düsseldorf; Heinz-Wilhelm Dehne, Bonn, all of Germany

[73] Assignee: Bayer Aktiengesellschaft, Leverkusen, Germany

[21] Appl. No.: 416,416

[22] Filed: Apr. 4, 1995

[30] Foreign Application Priority Data

Apr. 11, 1994 [DE] Germany .................. 44 12 358.2

[51] Int. Cl.$^6$ ............... A01N 43/653; C07D 249/08
[52] U.S. Cl. ............. 514/383; 514/184; 548/101; 548/267.2
[58] Field of Search .................. 514/184, 383; 548/267.2, 101

[56] References Cited

U.S. PATENT DOCUMENTS 5,140,035  8/1992  Scherkenbeck et al. ............ 514/383

FOREIGN PATENT DOCUMENTS 0123160  10/1984  European Pat. Off. .

*Primary Examiner*—Patricia L. Morris
*Attorney, Agent, or Firm*—Sprung Horn Kramer & Woods

[57] ABSTRACT

New cyclopropyl-ethyl-azoles of the formula

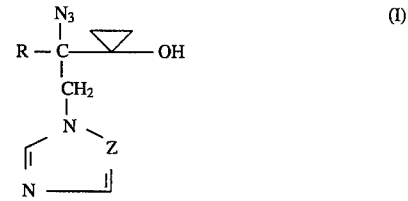

in which

R represents alkyl, alkenyl, alkinyl, cycloalkyl which is optionally substituted by alkyl, or optionally substituted aryl, optionally substituted aralkyl or optionally substituted aralkenyl, and Z represents a nitrogen atom or a CH group,
and addition products thereof with acids or metal salts are very effective for combating fungi.

Novel oxiranes of the formula

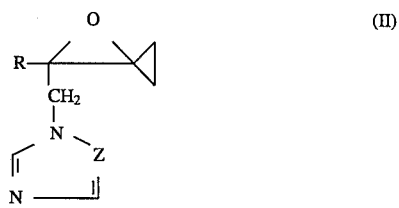

in which

R and Z have the abovementioned meanings,
are valuable intermediates.

5 Claims, No Drawings

CYCLOPROPYL-ETHYL-AZOLES

The present invention relates to new cyclopropyl-ethyl-azoles, to a process for their preparation, and to their use as fungicides. The invention furthermore relates to new intermediates and to a process for their preparation.

It has already been disclosed that certain hydroxyethyl-azolyl derivatives have fungicidal properties (cf. EP-OS (European Published Specification) 0 438 686 and EP-OS (European Published Specification) 0 123 160). For example, 1-(2-chlorophenyl)-2-(1-methoxy-cycloprop-1-yl)-3-(1,2,4-triazol-1-yl)-propan-2-ol and 1-(2-chlorophenyl)-2-(1,2,4-triazol-1-yl-methyl)-3,3-dimethyl-butan-2-ol can be used for combating fungi. The activity of these substances is good, but occasionally leaves something to be desired when low application rates are used.

New cyclopropyl-ethyl-azoles of the formula

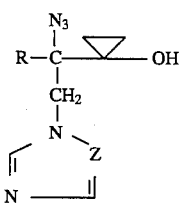

in which

R represents alkyl, alkenyl, alkinyl, cycloalkyl which is optionally substituted by alkyl, or optionally substituted aryl, optionally substituted aralkyl or optionally substituted aralkenyl, and Z represents a nitrogen atom or a CH group,
and their acid addition salts or metal salt complexes have now been found.

The substances according to the invention contain an asymmetrically substituted carbon atom. They can therefore be obtained in the form of optical isomers. The present invention relates to individual isomers and also to their mixtures.

Furthermore, it has been found that cyclopropyl-ethyl-azoles of the formula (I) and their acid addition salts and metal salt complexes are obtained when oxiranes of the formula

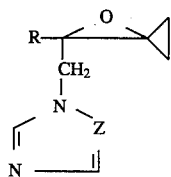

in which

R and Z have the abovementioned meanings,
are reacted with sodium azide in the presence of an additional diluent and if appropriate in the presence of a base and the product is worked up while adding water, and, if appropriate, the resulting compounds of the formula (I) are subsequently subjected to an addition reaction with an acid or a metal salt.

Finally, it has been found that the new cyclopropyl-ethyl-azoles of the formula (I) and their acid addition salts and metal salt complexes have very good fungicidal properties.

Surprisingly, the substances according to the invention show a better fungicidal activity than the prior-art compounds of the same direction of action which have the most similar constitution.

Formula (I) provides a general definition of the cyclopropyl-ethyl-azoles according to the invention.

R preferably represents straight-chain or branched alkyl having 1 to 8 carbon atoms, straight-chain or branched alkenyl having 2 to 8 carbon atoms, straight-chain or branched alkinyl having 2 to 8 carbon atoms, or cycloalkyl having 3 to 7 carbon atoms, it being possible for each of these cycloalkyl radicals to be monosubstituted to trisubstituted by identical or different alkyl substituents having 1 to 4 carbon atoms, or phenyl which can be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or phenylalkyl having 1 to 4 carbon atoms in the straight-chain or branched alkyl moiety, it being possible for the phenyl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or phenylalkenyl having 2 to 4 carbon atoms in the straight-chain or branched alkenyl moiety, it being possible for the phenyl moiety to be in each case monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano.

Z preferably also represents nitrogen or a CH group.

R particularly preferably represents straight-chain or branched alkyl having 1 to 6 carbon atoms, straight-chain or branched alkenyl having 2 to 6 carbon atoms, straight-chain or branched alkinyl having 2 to 6 carbon atoms, or cycloalkyl having 3 to 7 carbon atoms, it being possible for each of these radicals to be monosubstituted to trisubstituted by identical or different substituents from the series consisting of methyl and/or ethyl, or phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano, or phenylalkyl having 1 to 3 carbon atoms in the straight-chain or branched alkyl moiety, it being possible for the phenyl moiety to be in each case monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano, or phenylalkenyl having 2 to 4 carbon atoms in the straight-chain or branched alkenyl moiety, it being possible for the phenyl moiety to be in each case monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, methoxycarbonyl, ethoxycarbonyl, methoximinomethyl, 1-methoximinoethyl, nitro and/or cyano.

Z particularly preferably also represents nitrogen or a CH group.

Other preferred substances according to the invention are addition products of acids and cyclopropyl-ethyl-azoles of the formula (I) in which R and Z have the meanings mentioned above as being preferred.

The acids which can be subjected to an addition reaction preferably include hydrohalic acids such as, for example, hydrochloric acid and hydrobromic acid, in particular hydrochloric acid, furthermore phosphoric acid, nitric acid, sulphuric acid, mono- and bifunctional carboxylic acids and hydroxycarboxylic acids such as, for example, acetic acid, maleic acid, succinic acid, fumaric acid, tartaric acid, citric acid, salicylic acid, sorbic acid and lactic acid, and also sulphonic acids such as, for example, p-toluenesulphonic acid, 1,5-naphthalenedisulphonic acid or camphorsulphonic acid, and furthermore also saccharin and thiosaccharin.

Other preferred substances according to the invention are addition products of salts of metals of main groups II to IV and sub-groups I and II as well as IV to VIII of the Periodic Table of the Elements and cyclopropyl-ethyl-azoles of the formula (I) in which R and Z have the meanings mentioned above as being preferred.

Particularly preferred are salts of copper, zinc, manganese, magnesium, tin, iron and of nickel. Suitable anions of these salts are those which are derived from acids which lead to physiologically acceptable addition products. Particularly preferred acids of this type are, in this context, the hydrohalic acids such as, for example, hydrochloric acid and hydrobromic acid, and furthermore phosphoric acid, nitric acid and sulphuric acid.

Examples of substances according to the invention which may be mentioned are the cyclopropyl-ethyl-azoles listed in the table which follows.

TABLE 1

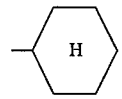

| R | Z |
|---|---|
| $-C_4H_9$-n | N |
| $-C_4H_9$-t | N |
| $-CH_2-CH=CH_2$ | N |
| $-C_4H_9$-n | CH |
| $-C_4H_9$-t | CH |
| $-CH_2-CH=CH-CH_3$ | N |
| $-CH_2-C{\equiv}CH$ | N |
| 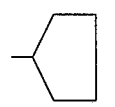 | N |
| 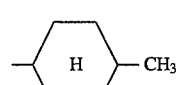 | N |
| 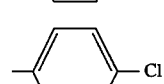 | N |
| 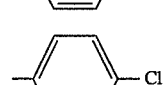 | N |
| 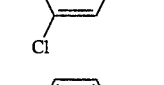 | N |
| 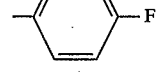 | N |
| 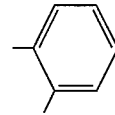 | N |
|  | N |

TABLE 1-continued
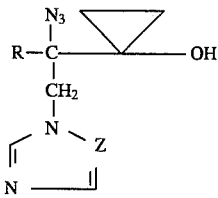
| R | Z |
|---|---|
| 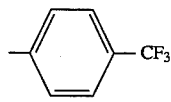 | N |
| 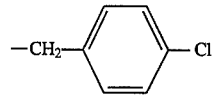 | N |
| 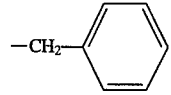 | N |
| 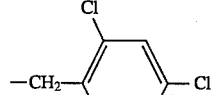 | N |
| 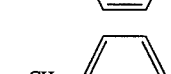 | N |
| 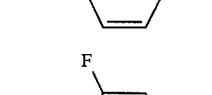 | N |
| 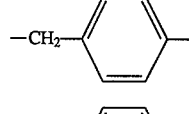 | N |
| 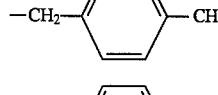 | N |
| 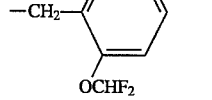 | N |
| 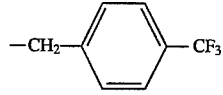 | N |
| 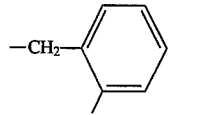 | N |
TABLE 1-continued
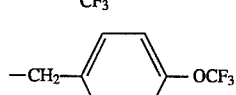
| R | Z |
|---|---|
| 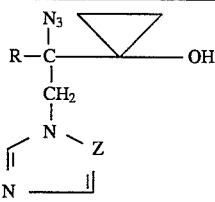 | N |
| 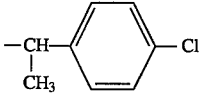 | N |
| 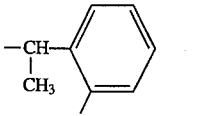 | N |
| 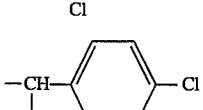 | N |
| 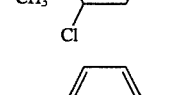 | N |
| 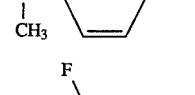 | N |
| 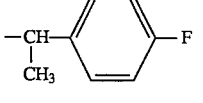 | N |
| 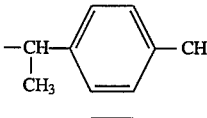 | N |
| 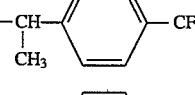 | N |
| 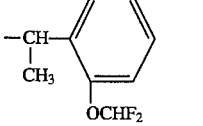 | N |
| 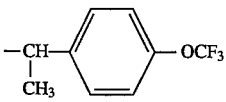 | N |

TABLE 1-continued $$\begin{array}{c} N_3 \\ | \\ R-C-\triangle-OH \\ | \\ CH_2 \\ | \\ N\diagdown Z \\ \| \quad \| \\ N \longrightarrow \end{array} \quad (I)$$

| R | Z |
|---|---|
| —CH₂—CH₂—C₆H₄—F | N |
| —CH₂—CH₂—C₆H₄—CH₃ | N |
| —CH₂—CH₂—C₆H₄—Cl | N |
| —CH=CH—C₆H₅ | N |
| —CH=CH—C₆H₄—Cl | N |
| —CH=CH—C₆H₄—CH₃ | N |
| —CH=CH—C₆H₄—F | N |
| —CH=CH—C₆H₄—CF₃ | N |
| —CH=CH—C₆H₄—OCF₃ | N |
| —CH=CH—C₆H₄—OCHF₂ | N |

If 3-(2-chlorobenzyl)-3-(1,2,4-triazol-1-yl-methyl)-2-oxaspiro[2,2]pentane and sodium azide are used as starting substances and aqueous sodium carbonate solution is used for the subsequent hydrolysis, the course of the process according to the invention can be illustrated by the following equation:

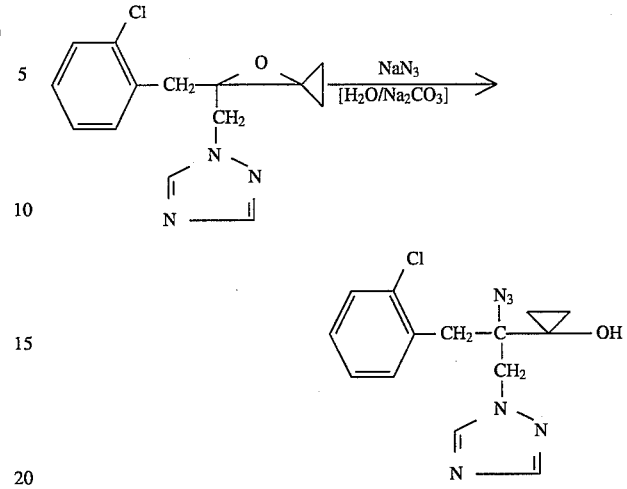

Formula (II) provides a general definition of the oxiranes required as starting substances for carrying out the process according to the invention. In this formula R and Z preferably have those meanings which have already been mentioned in connection with the description of the substances of the formula (I) according to the invention as being preferable for these radicals.

Examples of oxiranes of the formula (II) which may be mentioned are the substances listed in Table 2 which follows.

TABLE 2

$$\begin{array}{c} O \\ R-\overset{|}{\underset{CH_2}{C}}-\triangle \\ | \\ N\diagdown Z \\ \| \quad \| \\ N \longrightarrow \end{array} \quad (II)$$

| R | Z |
|---|---|
| —C₄H₉-n | N |
| —C₄H₉-t | N |
| —CH₂—CH=CH₂ | N |
| —C₄H₉-n | CH |
| —C₄H₉-t | CH |
| —CH₂—CH=CH—CH₃ | N |
| —CH₂—C≡CH | N |
| cyclohexyl | N |
| cyclopentyl | N |
| 4-methylcyclohexyl | N |
| 2-chlorophenyl | N |

TABLE 2-continued (II)

| R | Z |
|---|---|
| 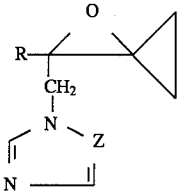 2,4-dichlorophenyl | N |
| 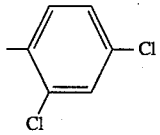 4-fluorophenyl | N |
| 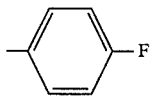 2,4-difluorophenyl | N |
| 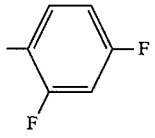 2-OCHF₂-phenyl | N |
| 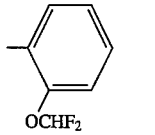 4-methylphenyl | N |
| 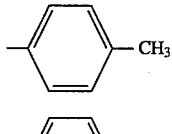 4-CF₃-phenyl | N |
| —CH₂— 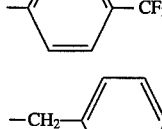 4-Cl-phenyl | N |
| —CH₂— 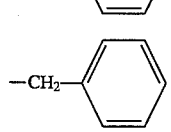 phenyl | N |
| —CH₂— 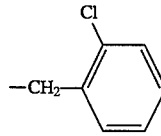 2,4-dichlorophenyl | N |
| —CH₂— 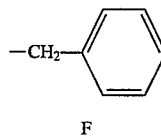 4-F-phenyl | N |
| —CH₂— 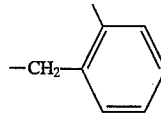 2,4-difluorophenyl | N |
| —CH₂—  4-CH₃-phenyl | N |
| —CH₂— 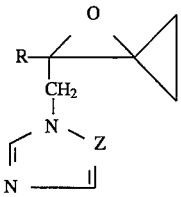 2-OCHF₂-phenyl | N |
| —CH₂— 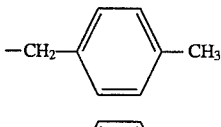 4-CF₃-phenyl | N |
| —CH₂— 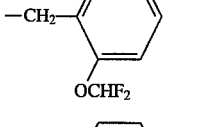 2-CF₃-phenyl | N |
| —CH₂— 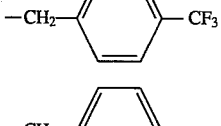 4-OCF₃-phenyl | N |
| —CH(CH₃)— 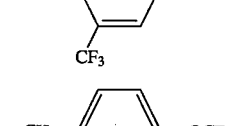 4-Cl-phenyl | N |
| —CH(CH₃)— 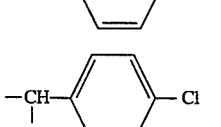 2-Cl-phenyl | N |
| —CH(CH₃)— 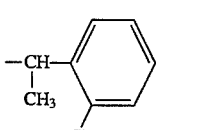 2,4-dichlorophenyl | N |
| —CH(CH₃)— 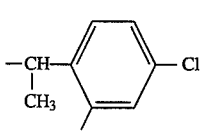 4-F-phenyl | N |
| —CH(CH₃)— 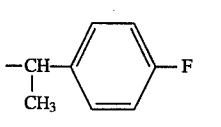 2,4-difluorophenyl | N |
| —CH(CH₃)— 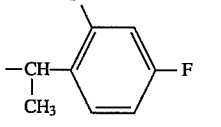 4-CH₃-phenyl | N |

TABLE 2-continued $$\text{(II)}$$

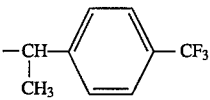

| R | Z |
|---|---|
| -CH(CH₃)-C₆H₄-CF₃ (para) | N |
| -CH(CH₃)-C₆H₄-OCHF₂ (ortho) | N |
| -CH(CH₃)-C₆H₄-OCF₃ (para) | N |
| -CH₂-CH₂-C₆H₄-Cl (para) | N |
| -CH₂-CH₂-C₆H₄-F (para) | N |
| -CH₂-CH₂-C₆H₄-CH₃ (para) | N |
| -CH₂-CH₂-C₆H₄-Cl (ortho) | N |
| -CH=CH-C₆H₅ | N |
| -CH=CH-C₆H₄-Cl (para) | N |
| -CH=CH-C₆H₄-CH₃ (para) | N |
| -CH=CH-C₆H₄-F (para) | N |
| -CH=CH-C₆H₄-CF₃ (para) | N |
| -CH=CH-C₆H₄-OCF₃ (para) | N |
| -CH=CH-C₆H₄-OCHF₂ (ortho) | N |

The oxiranes of the formula (II) are as yet not known. They can be prepared by reacting cyclopropyl-hydroxyethyl-azoles of the formula

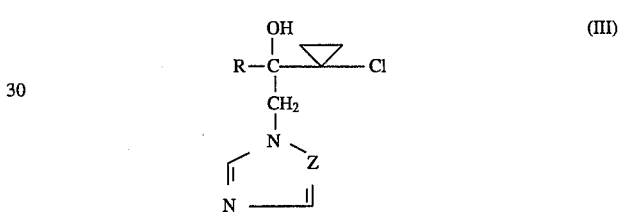

in which
R and Z have the abovementioned meanings,
in the presence of strong bases and in the presence of a diluent.

If 2-(1-chlorocyclopropyl)-1-(2-chlorophenyl)-2-hydroxy-3-(1,2,4-triazol-1-yl)-propane is used as starting substance and potassium tert-butylate as the strong base, the course of the process for the preparation of oxiranes of the formula (II) can be illustrated by the following equation:

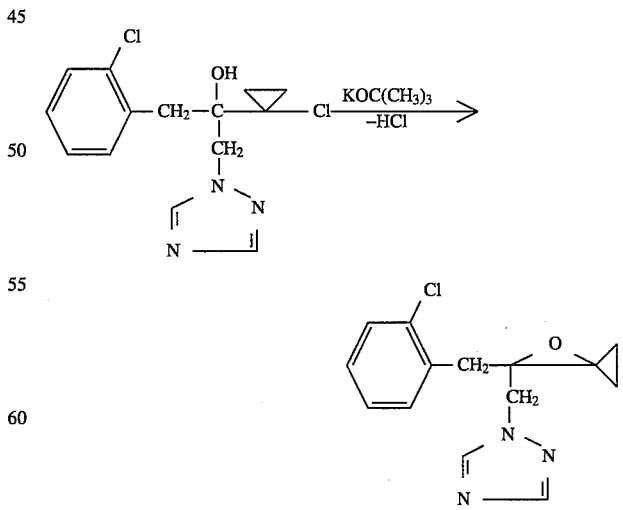

Formula (III) provides a general definition of the cyclopropyl-hydroxyethyl-azoles required as starting substances in the preparation of oxiranes of the formula (II). In this formula, R and Z preferably have those meanings which have already been mentioned in connection with the description of the substances of the formula (I) according to the invention as being preferable for these radicals.

The cyclopropyl-hydroxyethyl-azoles of the formula (III) are known or can be prepared by methods known in principle (cf. EP-OS (European Published Specification) 0 180 136, EP-OS (European Published Specification) 0 297 345, EP-OS (European Published Specification) 0 297 383, EP-OS (European Published Specification) 0 298 332, EP-OS (European Published Specification) 0 440 949 and EP-OS (European Published Specification) 0 470 463).

Suitable bases for carrying out the process for the preparation of oxiranes of the formula (II) are all customary strong inorganic and organic bases. The following can preferably be used: alkali metal alcoholates, such as sodium methylate, sodium ethylate and potassim tert-butylate, and furthermore alkali metal hydrides, such as sodium hydride.

Suitable diluents for carrying out the process for the preparation of oxiranes of the formula (II) are all inert organic solvents which are customary for reactions of this type. The following can preferably be used: alcohols, such as methanol, ethanol, propanol and tert-butanol, furthermore ethers, such as diethyl ether, 1,2-dimethoxyethane, tetrahydrofuran and dioxane, and moreover aliphatic, cycloaliphatic and aromatic hydrocarbons, such as pentane, hexane, cyclohexane, benzene, toluene and xylene.

When carrying out the process for the preparation of oxiranes of the formula (II), the reaction temperatures can be varied within a substantial range. In general, the process is carried out at temperatures between 0° C. and 100° C., preferably between 20° C. and 80° C.

In general, the process for the preparation of oxiranes of the formula (II) is carried out under atmospheric pressure. However, it is also possible to carry out the process under elevated or reduced pressure.

When carrying out the process for the preparation of oxiranes of the formula (II), 1 to 1.5 equivalents of strong base are generally employed per mole of cyclopropyl-hydroxyethyl-azole of the formula (III). Working-up is carried out by customary methods. In general, a procedure is followed in which the reaction mixture is washed with water, if appropriate after previously having been diluted with an organic solvent which is sparingly miscible with water, the organic phase is dried and concentrated, and, if appropriate, the product which remains is freed from any impurities which may be present by customary methods such as, for example, by chromatography.

When carrying out the process according to the invention for the preparation of cyclopropyl-ethyl-azoles of the formula (I), sodium azide is used as reactant. Water is only added at the working-up stage.

Suitable diluents for carrying out the process according to the invention for the preparation of substances of the formula (I) are all polar, aprotic organic solvents. The following can preferably be used: nitriles such as acetonitrile and propionitrile, furthermore amides, such as dimethylformamide and N-methyl-pyrrolidone, and moreover strongly polar solvents, such as dimethyl sulph-oxide.

Suitable bases for carrying out the process according to the invention for the preparation of substances of the formula (I) are all inorganic and organic acid-binding agents which are conventionally suitable for reactions of this type. The following can preferably be used: alkali metal carbonates, such as sodium carbonate and potassium carbonate, and moreover ammonium carbonate, and additionally tertiary amines, such as triethylamine and pyridine.

The reaction temperatures for carrying out the process according to the invention for the preparation of substances of the formula (I) can be varied within a substantial range. The process is generally carried out at temperatures between 20° C. and 130° C., preferably between 30° C. and 100° C.

The process according to the invention is generally carried out under atmospheric pressure. However, it is also possible to carry out the process under elevated or reduced pressure.

When carrying out the process according to the invention, 1 mol of sodium azide, or else an excess, is generally employed per mole of oxirane of the formula (II). Working-up is carried out by customary methods. Generally, a procedure is followed in which the reaction mixture is washed with water, if appropriate in the presence of an alkali metal base and, if appropriate, after previously having been diluted with an organic solvent which is sparingly miscible with water, the organic phase is dried and concentrated and, if appropriate, the product which remains is freed from any impurities which may be present by customary methods, for example by chromatography.

The cyclopropyl-ethyl-azoles of the formula (I) according to the invention can be converted into acid addition salts or metal salt complexes.

Acids which are preferably suitable for the preparation of acid addition salts of the compounds of the formula (I) are those which have already been mentioned in connection with the description of the acid addition salts according to the invention as being preferred acids.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and, if appropriate, purified by washing with an inert organic solvent.

Salts of metals which are preferably suitable for the preparation of metal salt complexes of the compounds of the formula (I) are those which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtration, and, if appropriate, purified by recrystallization.

The active compounds according to the invention have a powerful microbicidal action and can be employed as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation:
Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*

Peronospora species, such as *Peronospora pisi* or *P. brassicae;*

Erysiphe species, such as *Erysiphe graminis;*

Sphaerotheca species, such as *Sphaerotheca fuliginea;*

Podosphaera species, such as *Podosphaera leucotricha;*

Venturia species, such as *Venturia inaequalis;*

Pyrenophora species, such as *Pyrenophora teres* or *P. graminea;*

(conidia form: Drechslera, syn: Helminthosporium);

Cochliobolus species, such as *Cochliobolus sativus;*

(conidia form: Drechslera, syn: Helminthosporium);

Uromyces species, such as *Uromyces appendiculatus;*

Puccinia species, such as *Puccinia recondita;*

Tilletia species, such as *Tilletia caries;*

Ustilago species, such as *Ustilago nuda* or *Ustilago avenae;*

Pellicularia species, such as *Pellicularia sasakii;*

Pyricularia species, such as *Pyricularia oryzae;*

Fusarium species, such as *Fusarium culmorum;*

Botrytis species, such as *Botrytis cinerea;*

Septoria species, such as *Septoria nodorum;*

Leptosphaeria species, such as *Leptosphaeria nodorum;*

Cercospora species, such as *Cercospora canescens;*

Alternaria species, such as *Alternaria brassicae;*

Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seed, and of the soil.

The active compounds according to the invention are particularly suitable for combating diseases of cereals, such as Erysiphe, Leptosphaeria and Fusarium, and for combating Plasmopara, Venturia and Podosphaera in fruit growing, viticulture and vegetable growing. Moreover, they can be employed against rice diseases such as *Pyricularia oryzae*, and they also have a good and broad in-vitro action.

The substances according to the invention can be converted into the customary formulations, such as solutions, emulsions, suspensions, powders, foams, pastes, granules, aerosols, very fine capsules in polymeric substances and in coating compositions for seed, as well as ULV formulations.

These formulations are produced in a known manner, for example by mixing the active compounds with extenders, that is, liquid solvents, liquefied gases under pressure, and/or solid carriers, optionally with the use of surface-active agents, that is, emulsifying agents and/or dispersing agents and/or foam-forming agents. In the case of the use of water as an extender, organic solvents, such as alcohols, can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethyl-ene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose, natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in the formulations as a mixture with known fungicides, bactericides, acaricides, nematicides or insecticides, for example so as to widen the spectrum of action or to prevent the build-up of resistance. In some cases, synergism is observed.

Examples of suitable substances for the mixtures are those which follow.

Fungicides:

2-aminobutane; 2-anilino-4-methyl-6-cyclopropyl-pyrimidine; 2',6'-dibromo-2-methyl-4'-trifluoromethoxy-4'-trifluoromethyl-1,3-thiazole-5-carboxanilide; 2,6-dichloro-N-(4-trifluoromethylbenzyl)benzamide; (E)-2-methoximino-N-methyl-2-(2-phenoxyphenyl)-acetamide; 8-hydroxyquinoline sulphate; methyl (E)-2-{2-[6-(2-cyanophenoxy)-pyrimidin-4-yloxy]phenyl}-3-methoxyacrylate; methyl (E)-methoximino [alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, chinomethionate (quinomethionate), chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetylaluminium, fthalide, fuberidazole, furalaxyl, furmecyclox, guazatine,
hexachlorobenzene, hexaconazole, hymexazole,
imazalil, imibenconazole, iminoctadine, iprobenfos (IBP), iprodione, isoprothiolane,
kasugamycin, copper preparations such as: copper hydroxide, copper naphthenate, copper oxychloride, copper sulphate, copper oxide, oxine-copper and Bordeaux mixture,
mancopper, mancozeb, maneb, mepanipyrim, mepronil, metalaxyl, metconazole, methasulfocarb, methfuroxam, metiram, metsulfovax, myclobutanil,
nickel dimethyldithiocarbamate, nitrothal-isopropyl, nuarimol,
ofurace, oxadixyl, oxamocarb, oxycarboxin,
pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon,
quintozene (PCNB),
sulphur and sulphur preparations,
tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole,
validamycin A, vinclozolin,
zineb, ziram.
Bactericides:
bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.
Insecticides/Acaricides/Nematicides:
abamectin, AC 303 630, acephate, acrinathrin, alanycarb, aldicarb, alphamethrin, amitraz, avermectin, AZ 60541, azadirachtin, azinphos A, azinphos M, azocyclotin,
Bacillus thuringiensis, bendiocarb, benfuracarb, bensultap, beta-cyfluthrin, bifenthrin, BPMC, brofenprox, bromophos A, bufencarb, buprofezin, butocarboxin, butylpyridaben,
cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine,
deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton,
edifenphos, emamectin, esfenvalerate, ethiofencarb, ethion, ethofenprox, ethoprophos, etrimphos,
fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb,
HCH, heptenophos, hexaflumuron, hexythiazox,
imidacloprid, iprobenfos, isazophos, isofenphos, isoprocarb, isoxathion, ivemectin,
lambda-cyhalothrin, lufenuron,
malathion, mecarbam, mervinphos, mesulfenphos, metaldehyde, methacrifos, methamidophos, methidathion, methiocarb, methomyl, metolcarb, milbemectin, monocrotophos, moxidectin,
naled, NC 184, NI 25 nitenpyram,
omethoate, oxamyl, oxydemethon M, oxydeprofos,
parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen,
quinalphos,
RH 5992,
salithion, sebufos, silafluofen, sulfotep, sulprofos,
tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb,
vamidothion, XMC, xylylcarb, zetamethrin.
A mixture with other known active compounds, such as herbicides, or with fertilizers and growth regulators is also possible.

The active compounds can be used as such or in the form of their formulations or the use forms prepared therefrom, such as ready-to-use solutions, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range: they are, in general, between 1 and 0.0001% by weight, preferably between 0.5 and 0.001% by weight.

In the treatment of seed, amounts of active compound of 0.001 to 50 g per kilogram of seed, preferably 0.01 to 10 g, are generally required.

For the treatment of the soil, active compound concentrations of 0.00001 to 0.1% by weight, preferably 0.0001 to 0.02% by weight, are required at the place of action.

Preparation and use of active compounds according to the invention are illustrated by the examples which follow.

PREPARATION EXAMPLES

Example 1

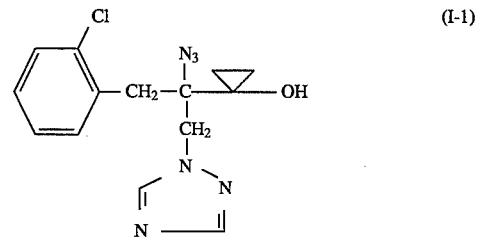

A mixture of 2.76 g (10 mmol) of 3-(2-chlorobenzyl)-3-(1,2,4-triazol-1 -yl-methyl)-2-oxa-spiro[2,2]pentane, 0.39 g (6 mmol) of sodium azide and 20 ml of absolute dimethylformamide is heated for 3 hours at 80° C., with stirring. Then, the reaction mixture is treated with ethyl acetate and extracted repeatedly by shaking with saturated aqueous sodium carbonate solution. The organic phase is dried over sodium sulphate and concentrated under reduced pressure. This gives 3.3 g of a crude product which is chromatographed over 300 g of silica gel using ethyl acetate as the eluent. After the eluate has been concentrated, 1.3 g (41% of theory) of 2-azido-2-(1-hydroxy-cyclopropyl-1-yl )-1-(2-chlorophenyl)-3-(1,2,4-triazol-1-yl)-propane are obtained in the form of a solid substance of melting point 137°–139° C.

PREPARATION OF STARTING SUBSTANCES

Example 2

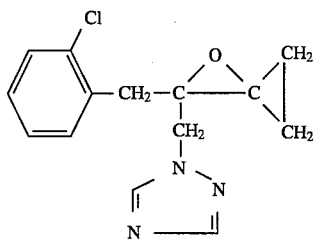
(II-1)

A mixture of 3.12 g (10 mmol) of 2-(1-chlorocyclopropyl)-1-(2-chlorophenyl)-2 -hydroxy-3-(1,2,4-triazol-1-yl)-propane, 1.12 g (10 mmol) of potassium tert-butylate and 50 ml of absolute tert-butanol is stirred for 25 hours at 60° C. Then, the reaction mixture is diluted with ethyl acetate and washed repeatedly with water. The organic phase is dried over sodium sulphate and concentrated under reduced pressure. This gives 3.29 g of a crude product which is chromatographed over 300 g of silica gel using ethyl acetate as the eluent. After the eluate has been concentrated, 1.3 g (47% of theory) of 3-(2-chlorobenzyl)-3-(1,2,4-triazol-1-yl-methyl)-2 -oxa-spiro[2,2]-pentaneare obtained in the form of an oil.

$^1$H NMR spectrum (200 MHz, CDCl$_3$, TMS):

δ=0.7–0.95 (m, 4H); 3.3 (s, 2H); 4.55 (AB, 2H); 7.2–7.4 (m, 4H); 7.9 (s, 1H); 8.1 (s, 1H) ppm GC/MS (Ci): 276 (M+H$^+$, 100%)

Example 3

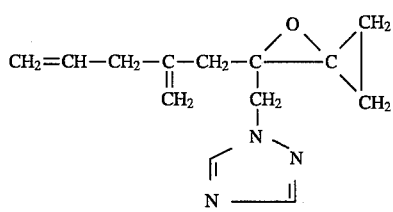
(II-2)

A mixture of 1.34 g (5 mmol) of 6-(1-chlorocyclopropyl)-6-hydroxy-4-methylene-7 -(1,2,4-triazol-1-yl)-hept-1-ene, 0.56 g (5 mmol) of potassium tert-butylate and 30 ml of absolute tert-butanol is stirred for 22 hours at 60° C. The reaction mixture is then diluted with ethyl acetate and washed repeatedly with water. The organic phase is dried over sodium sulphate and concentrated under reduced pressure. This gives 1.1 g of a crude product which is chromatographed over 300 g of silica gel using ethyl acetate as the eluent. After the eluate has been concentrated, 0.8 g (70% of theory) of 3-(2-methylene-pent-4-enyl)-3-(1,2,4-triazol-1 -yl -methyl)-2-oxa-spiro[2,2]-pentane is obtained in the form of an oil.

$^1$H NMR spectrum (200 MHz, CDCl$_3$, TMS):

δ (ppm)=0.8–1.1 (m, 4H); 2.45 (AB, 2H); 2.7 (AB, 2H); 4.55 (s, 2H); 5.0 (m, 4H); 5.8 (m, 1H); 7.95 (s, 1H); 8.15 (s, 1H)

GC/MS (Ci): 232 (M+H$^+$, 100%)

Example 4

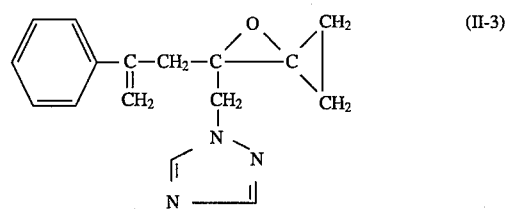
(II-3)

A mixture of 1.52 g (5 mmol) of 4-(1-chloro-cyclopropyl)-4 -hydroxy-2-phenyl-5-(1,2,4-triazol-1-yl)-pent-1-ene, 0.67 g (6 mmol) of potassium tert-butylate and 50 ml of absolute tetrahydrofuran is stirred for 5 hours at 40° C. Then, the reaction mixture is diluted with ethyl acetate and washed repeatedly using saturated aqueous sodium carbonate solution. The organic phase is dried over sodium sulphate and concentrated under reduced pressure. This gives 1.3 g of a crude product which is chromatographed over 200 g of silica gel using ethyl acetate as the eluent. After the eluate has been concentrated, 0.5 g (37% of theory) of 3-(2-phenyl-prop-1-en-3-yl)-3 -(1,2,4-triazol-1-yl-methyl)-2-oxa-spiro[2,2]-pentane is obtained in the form of an oil.

GC/MS(Ci): 268 (M+H$^+$, 100%)

Example 5

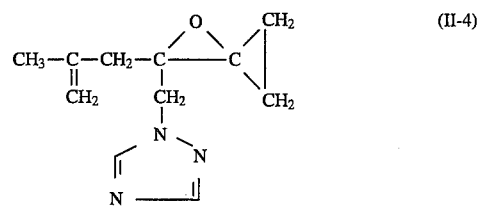
(II-4)

The compound of the formula (II-4) is also prepared by the method given in Example 4. The substance is obtained in the form of an oil.

GC/MS (Ci): 206 (M+H$^+$, 100%)

USE EXAMPLES

Example A

Erysiphe test (barley)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown.

After the spray coating has dried on, the plants are dusted with spores of *Erysiphe graminis* f.sp. *hordei*.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a degree of effectiveness of 100% is shown by compound (I-1) according to the invention at an application rate of 250 g/ha.

Example B

*Gibberella zeae* test (barley)/protective (syn. *Fusarium graminearum*)

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown.

After the spray coating has dried on, the plants are dusted with a conidia suspenion of *Gibberella zeae*.

The plants are placed in a greenhouse under translucent incubation cloches at a temperature of about 20° C. and a relative atmospheric humidity of about 100%.

Evaluation is carried out 4 days after the inoculation.

In this test, a degree of effectiveness of 100% is shown by compound (I-1) according to the invention at an application rate of 250 g/ha.

Example C

Plasmopara test (vines)/protective

Solvent: 4.7 parts by weight of acetone

Emulsifier: 0.3 part by weight of alkyl-aryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Plasmopara viticola* and then remain in a humidity chamber at 20° to 22° C. and 100 % relative atmospheric humidity for 1 day. The plants are then placed in a greenhouse at 21° C. and 90% atmospheric humidity for 5 days. The plants are then moistened and placed in a humidity chamber for 1 day.

Evaluation is carried out 6 days after the inoculation.

In this test, a degree of effectiveness of over 90% is shown by compound (I-1) according to the invention at an application rate of 10 ppm.

It will be understood that the specification and examples are illustrative, but not limitative of the present invention and that other embodiments within the spirit and scope of the invention will suggest themselves to those skilled in the art.

What is claimed is:

1. A cyclopropyl-ethyl-azole of the formula $$R-\underset{\underset{\underset{N}{\overset{|}{\underset{N}{\overset{|}{\text{CH}_2}}}}}{\overset{N_3}{\overset{|}{C}}}}{\overset{}{\bigtriangledown}}-OH \quad (I)$$

in which

R represents straight-chain or branched alkyl having 1 to 8 carbon atoms, straight-chain or branched alkenyl having 2 to 8 carbon atoms, Straight-chain or branched alkinyl having 2 to 8 carbon atoms, or cycloalkyl having 3 to 7 carbon atoms, wherein each of these cycloalkyl radicals is optionally monosubstituted to trisubstituted by identical or different alkyl substituents having 1 to 4 carbon atoms, or phenyl which can be monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkoxy having 1 to 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety nitro and cyano, or phenylalkyl having 1 to 4 carbon atoms in the straight-chain or branched alkyl moiety, wherein the phenyl moiety is optionally monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 to 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxymoiety, alkoximinoalkyl having 1 to 4 carbon atoms in the alkoxy moiety and 1 to 4 carbon atoms in the alkyl moiety, nitro and cyano, or phenylalkenyl having 2 to 4 carbon atoms in the straight-chain or branched alkenyl moiety, wherein the phenyl moiety is optionally monosubstituted to trisubstituted by identical or different substituents selected from the group consisting of halogen, alkyl having 1 to 4 carbon atoms, alkoxy having 1 to 4 carbon atoms, alkylthio having 1 to 4 carbon atoms, halogenoalkyl having 1 to 2 carbon atoms and 1 to 5 identical or different halogen atoms, halogenoalkoxy having 1 to 2 carbon atoms and 1 to 5 identical or different halogen atoms, halogenoalkylthio having 1 to 2 carbon atoms and 1 to 5 identical or different halogen atoms, halogenoalkylthio having 1 to 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxymoiety, alkoximinoalkyl having 1 to 4 carbon atoms in the alkoxy moiety and 1 to 4 carbon atoms in the alkyl moiety, nitro and cyano, or an addition product thereof with an acid or metal salt.

2. A compound according to claim 1, wherein such compound is 2-azido-2-(1-hydroxy-cycloprop-1-yl)-1-(2-chlorophenyl)-3-(1,2,4-triazol-1-yl)-propane of the formula

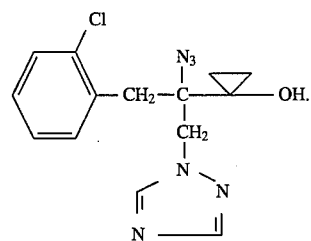

3. A fungicidal composition comprising a fungicidally effective amount of a compound or addition product according to claim 1 and an inert diluent.

4. A method of combating fungi, which method comprises applying to such fungi or to their habitat a fungicidally effective amount of a compound or addition product according to claim 1.

5. A method according to claim 4, wherein such compound is 2-azido-2-(1-hydroxy-cycloprop-1-yl)-1-(2-chlorophenyl)-3-(1,2,4-triazol-1 -yl)-propane.

* * * * *